US012186193B2

(12) United States Patent
Kazantsev et al.

(10) Patent No.: US 12,186,193 B2
(45) Date of Patent: Jan. 7, 2025

(54) TITANIUM MATRIX BASED ON A TENSION-FREE METAL WARP KNIT FABRIC FOR GUIDED TISSUE REGENERATION

(71) Applicant: Titanium Textiles AG, Bentwisch (DE)

(72) Inventors: Anton Anatolevich Kazantsev, g. Ekaterinburg (RU); Vladimir Andreevich Zavaruev, Moscow (RU); Ajrat Auhatovich Yusupov, Sverdlovskaya oblast (RU); Elena Nikolaevna Kolesnikova, Moscow (RU)

(73) Assignee: TITANIUM TEXTILES AG, Bentwisch (DE)

( * ) Notice: Subject to any disclaimer, the term of this patent is extended or adjusted under 35 U.S.C. 154(b) by 1056 days.

(21) Appl. No.: 16/977,267

(22) PCT Filed: Mar. 1, 2018

(86) PCT No.: PCT/RU2018/000119
§ 371 (c)(1),
(2) Date: Oct. 2, 2020

(87) PCT Pub. No.: WO2019/156588
PCT Pub. Date: Aug. 15, 2019

(65) Prior Publication Data
US 2021/0154360 A1    May 27, 2021

(51) Int. Cl.
*A61F 2/28*     (2006.01)
*A61C 8/02*     (2006.01)
(Continued)

(52) U.S. Cl.
CPC .......... *A61F 2/2846* (2013.01); *A61C 8/0006* (2013.01); *A61F 2/0063* (2013.01);
(Continued)

(58) Field of Classification Search
CPC ..... A61F 2/2846; A61C 8/0006; A61L 27/06; A61L 27/56; A61L 2430/02; A61L 2430/12; D04B 21/08; D10B 2403/02
See application file for complete search history.

(56) References Cited

U.S. PATENT DOCUMENTS 6,214,049 B1    4/2001   Gayer et al.
6,709,379 B1    3/2004   Brandau et al.
(Continued)

FOREIGN PATENT DOCUMENTS

CN       101766539 A       7/2010
CN       101766541 A       7/2010
(Continued)

OTHER PUBLICATIONS

Notice of Allowance of KR Application No. 10-2020-7028319 dated Oct. 17, 2023 and English translation, 8 pages.
(Continued)

*Primary Examiner* — Bruce E Snow
(74) *Attorney, Agent, or Firm* — Muncy, Geissler, Olds & Lowe, P.C.

(57) ABSTRACT

The invention relates to medicine and, more particularly to surgery and oral surgery. A titanium matrix based on a tension-free metal warp knit fabric for guided tissue regeneration is made of a warp-knitted mesh fabric formed from titanium threads, the structure of the mesh fabric being in the form of a combined, plain, two-bar metal warp knit fabric formed on the basis of primary and derived weaves and having alternating wales consisting of one and two titanium threads respectively, wherein the titanium threads have a contoured surface. The technical result is: a decrease in the elasticity and an increase in the plasticity of the material, allowing the set dimensions of an implant to be preserved (Continued)

after the removal of all loads on the material; an increase of the adhesion of the matrix to the wound bed; delineation of the growth of the mucous membrane and of the bone tissue; good quality formation of the necessary volume of bone tissue for the subsequent insertion of dental implants; minimal likelihood of biomechanical incompatibility between the warp knit fabric and the mucous membrane, and reduced risk of trauma. 8 d.c., 7 ill.

The invention relates to medicine and, more particularly to surgery and oral surgery. A titanium matrix based on a tension-free metal warp knit fabric for guided tissue regeneration is made of a warp-knitted mesh fabric formed from titanium threads, the structure of the mesh fabric being in the form of a combined, plain, two-bar metal warp knit fabric formed on the basis of primary and derived weaves and having alternating wales consisting of one and two titanium threads respectively, wherein the titanium threads have a contoured surface. The technical result is: a decrease in the elasticity and an increase in the plasticity of the material, allowing the set dimensions of an implant to be preserved after the removal of all loads on the material; an increase of the adhesion of the matrix to the wound bed; delineation of the growth of the mucous membrane and of the bone tissue; good quality formation of the necessary volume of bone tissue for the subsequent insertion of dental implants; minimal likelihood of biomechanical incompatibility between the warp knit fabric and the mucous membrane, and reduced risk of trauma. 8 d.c., 7 ill.

9 Claims, 3 Drawing Sheets (51) Int. Cl.
  *A61F 2/00* (2006.01)
  *A61L 27/06* (2006.01)
  *A61L 27/56* (2006.01)
  *D04B 21/08* (2006.01)

(52) U.S. Cl.
  CPC .............. *A61L 27/06* (2013.01); *A61L 27/56* (2013.01); *D04B 21/08* (2013.01); *A61L 2430/02* (2013.01); *A61L 2430/12* (2013.01); *D10B 2403/02* (2013.01); *D10B 2509/00* (2013.01)

(56) References Cited

U.S. PATENT DOCUMENTS

| | | | |
|---|---|---|---|
| 6,911,046 B2 | 6/2005 | Schulter | |
| 9,347,157 B2* | 5/2016 | Zhang | D04B 21/18 |
| 9,732,321 B2 | 8/2017 | Bassett et al. | |
| 2003/0068595 A1 | 4/2003 | Pitnick et al. | |
| 2006/0008773 A1 | 1/2006 | Liao | |
| 2006/0073181 A1 | 4/2006 | Kuboki | |
| 2007/0154621 A1 | 7/2007 | Raad | |
| 2008/0274671 A1 | 11/2008 | O'Donoghue et al. | |
| 2008/0294271 A1 | 11/2008 | Bjursten et al. | |
| 2008/0318044 A1 | 12/2008 | Tian et al. | |
| 2009/0030504 A1 | 1/2009 | Weber et al. | |
| 2009/0112310 A1 | 4/2009 | Zhang | |
| 2009/0220561 A1 | 9/2009 | Jin et al. | |
| 2010/0303722 A1 | 12/2010 | Jin et al. | |
| 2010/0311615 A1 | 12/2010 | Qu et al. | |
| 2011/0085968 A1 | 4/2011 | Jin et al. | |
| 2011/0125263 A1 | 5/2011 | Webster et al. | |
| 2011/0159070 A1 | 6/2011 | Jin et al. | |
| 2014/0147814 A1 | 5/2014 | Collins et al. | |
| 2014/0371687 A1 | 12/2014 | Mendelsohn et al. | |
| 2016/0153127 A1* | 6/2016 | Avio | D04B 21/06 442/164 |
| 2016/0220496 A1 | 8/2016 | Roorda | |
| 2016/0220730 A1 | 8/2016 | Procter et al. | |
| 2017/0201031 A1* | 7/2017 | Gelb | H01Q 15/168 |
| 2017/0274089 A1 | 9/2017 | Mendelsohn et al. | |
| 2021/0154360 A1* | 5/2021 | Kazantsev | D04B 21/08 |
| 2023/0349079 A1* | 11/2023 | Fedner | D04B 1/24 |

FOREIGN PATENT DOCUMENTS

| | | |
|---|---|---|
| CN | 101785880 A | 7/2010 |
| CN | 102058904 A | 5/2011 |
| CN | 103143068 A | 6/2013 |
| CN | 103357070 A | 10/2013 |
| CN | 104274862 A | 1/2015 |
| CN | 104826159 A | 8/2015 |
| CN | 104941002 A | 9/2015 |
| CN | 105935317 A | 9/2016 |
| CN | 106110391 A | 11/2016 |
| CN | 106377495 A | 2/2017 |
| CN | 106390207 A | 2/2017 |
| CN | 106729964 A | 5/2017 |
| CN | 206198351 U | 5/2017 |
| CN | 106937896 A | 7/2017 |
| CN | 107569716 A | 1/2018 |
| DE | 10040590 C2 | 7/2002 |
| DE | 10247397 B3 | 1/2004 |
| DE | 10311990 B4 | 4/2006 |
| DE | 202006015415 U1 | 11/2006 |
| DE | 202006015416 | 11/2006 |
| DE | 10219853 B4 | 8/2009 |
| DE | 102008018202 A1 | 10/2009 |
| DE | 202013006283 U1 | 4/2014 |
| DE | 202014102531 U1 | 7/2014 |
| DE | 202015102114 U1 | 5/2015 |
| DE | 102008037204 B4 | 1/2016 |
| DE | 10301850 B4 | 5/2017 |
| DE | 102015107291 B4 | 6/2017 |
| DE | 102016107791 B4 | 3/2018 |
| EP | 0880946 A1 | 12/1998 |
| EP | 0746269 B1 | 3/2000 |
| EP | 0706876 B1 | 7/2000 |
| EP | 0839221 B1 | 9/2000 |
| EP | 0773751 B1 | 10/2001 |
| EP | 0755664 B1 | 12/2002 |
| EP | 0986347 B1 | 12/2003 |
| EP | 1035808 B1 | 3/2004 |
| EP | 1309294 B1 | 7/2005 |
| EP | 1407727 B1 | 8/2005 |
| EP | 1219246 B1 | 3/2006 |
| EP | 1669032 A2 | 6/2006 |
| EP | 0788802 B1 | 7/2006 |
| EP | 1552855 A1 | 8/2008 |
| EP | 1683501 B1 | 10/2008 |
| EP | 1997521 A1 | 12/2008 |
| EP | 1629796 B1 | 3/2009 |
| EP | 2062554 A1 | 5/2009 |
| EP | 2153787 A1 | 2/2010 |
| EP | 2078512 B1 | 7/2012 |
| EP | 2567716 A1 | 3/2013 |
| EP | 1551332 B1 | 10/2013 |
| EP | 2163268 B1 | 1/2014 |
| EP | 2687188 | 1/2014 |
| EP | 2764877 B1 | 4/2016 |
| EP | 1800699 B1 | 4/2017 |
| EP | 2765216 B1 | 11/2017 |
| EP | 1852135 B1 | 4/2018 |
| EP | 2714974 B1 | 6/2019 |
| JP | 2010215438 A2 | 9/2010 |
| JP | 2016534241 A | 11/2016 |
| KR | 20110113589 A | 10/2011 |
| KR | 20120120784 A | 11/2012 |
| KR | 101297814 B1 | 8/2013 |
| KR | 20140035733 A | 3/2014 |
| KR | 20160070055 A | 6/2016 |
| KR | 20200126380 A | 11/2020 |
| KR | 102459873 B1 | 10/2022 |
| KR | 102459884 B1 | 10/2022 |

(56) References Cited

FOREIGN PATENT DOCUMENTS

| | | |
|---|---|---|
| RU | 117087 U1 | 6/2012 |
| RU | 121735 U1 | 11/2012 |
| RU | 2469744 C1 | 12/2012 |
| RU | 128098 U1 | 5/2013 |
| RU | 152119 U1 | 5/2015 |
| RU | 2578359 C1 | 3/2016 |
| WO | 9930632 | 6/1999 |
| WO | 0162180 A1 | 8/2001 |
| WO | 03037209 A1 | 5/2003 |
| WO | 03042440 A2 | 5/2003 |
| WO | 2005114120 A2 | 12/2005 |
| WO | 2006053044 A1 | 5/2006 |
| WO | 2007030274 A2 | 3/2007 |
| WO | 2008040408 A1 | 4/2008 |
| WO | 2008040409 A1 | 4/2008 |
| WO | 09032956 | 3/2009 |
| WO | 10016622 A1 | 2/2010 |
| WO | 2010097635 A1 | 9/2010 |
| WO | 2010117641 A2 | 10/2010 |
| WO | 2011060177 A2 | 5/2011 |
| WO | 2011069161 A1 | 6/2011 |
| WO | 2011136824 A1 | 11/2011 |
| WO | 2012160308 A1 | 11/2012 |
| WO | 2014097603 A1 | 6/2014 |
| WO | 2014098779 A2 | 6/2014 |
| WO | 2014107601 A1 | 7/2014 |
| WO | 14148765 A1 | 9/2014 |
| WO | 2014181144 A1 | 11/2014 |
| WO | 2015010643 A1 | 1/2015 |
| WO | WO-2015017032 A1 | 2/2015 |
| WO | 2016024942 A1 | 2/2016 |
| WO | 2016140638 A1 | 9/2016 |
| WO | 16171310 | 10/2016 |
| WO | 2017180318 A1 | 10/2017 |
| WO | 18107092 A1 | 6/2018 |
| WO | WO-2019156588 A1 * | 8/2019 ........... A61C 8/0006 |

OTHER PUBLICATIONS

Pivkina, Svetlana Ivanovna, "Development of Technology of Knitted Fabrics and Products Made of Titanium Threads for Endoprostheses," Dissertations for the degree of Candidate of Technical Sciences, Russian State University named after A.N. Kosygin (Technologies. Design. Art), Moscow, 2017, 226 pages.

Pivkina, Svetlana Ivanovna, "Development of Technology of Knitted Fabrics and Products Made of Titanium Threads for Endoprostheses," Dissertations for the degree of Candidate of Technical Sciences, Russian State University named after A.N. Kosygin (Technologies. Design. Art), Moscow, 2017, 17 pages.

"T-Barrier Titanium Membrane," B&B Dental Implant Company, https://www.bebdental.it/ru/ регенера ция-кост и/титано вые-мем браны-t-barrier (retrieved from the internet; Wayback machine snapshots Aug. 14, 2017 and Oct. 10, 2017), 2 pages.

Kolpakov, A.A., Ruchkin, V.I., Kolpakova, G.I. (2010) Proceedings of the VII Conference—Current issues in herniology, Oct. 20-21, 2010, 137-140.

Kolpakov, A.A. (2011). Combined prosthesis for surgical treatment of primary ventral hernias. VIII Conference—Current issues in herniology, Nov. 1-2, 2011, 113.

Kolpakov, A.A. (2011). Clinical comparison of the results of using Prolene, nickelid titanium and titanium meshes in combined abdominal wall defect repair. VIII Conference—Current issues in herniology, Nov. 1-2, 2011, 112.

Parshikov, V. V., Samsonov, A. V., Khodak, V. A., Petrov, V. V., Romanov, R. V., Samsonov, A. A., Gradusov, V. P., Tsybusov, S. N., Baburin, A. B., & Kazantsev, A. A. (2011). Abdominal wall plasty with Titanium Silk meshes. VIII Conference—Current issues in herniology, Nov. 1-2, 2011, 157-159.

Lazovsky, S.D., Karlov, D.I., Kazantsev A.A. (2012) Case of reconstruction of the tendon of the rectus femoris muscle with titanium mesh for reinforcing plasty of soft tissues 'Titanium Silk' Demidovskaya Central District Hospital, Nizhny Tagil, Russia, NPF Temir, Yekaterinburg, Russia.

Parshikov, V. V., Samsonov, A. V., Romanov, R. V., Gradusov, V. P., Samsonov, A. A., Khodak, V. A., Petrov, V. V., Tsybusov, S. N., Baburin, A. B., Kihlyarov, P. V., & Kazantsev, A. A. (2012). The first experience of the plastics of the abdominal wall with endoprostheses from Titanium Silk. Medical Almanac, 1(20), 107-110.

Parshikov, V. V., Khodak, V. A., Petrov, V. V., Dvornikov, A. V., Mironov, A. A., Samsonov, A. A., & Romanov, R. V. (2012). Retromuscular plasty of abdominal wall using mesh. Fundamental Research, (7), 159-163.

Chernov, A. V., Irianov, Y. M., Radchenko, S. A., Chernov, V. F., & Irianova, T. Y. (2012). Studying the integration features of different biomaterials in organism soft and bone tissues. Genius of Orthopedics, 1, 97-101.

Volova, L.T., Ponomareva, J.V., & Rozenbaum, A.Y. (2012). The value of testing in cell culture for low toxicity effect detection of medical devices. Bulletin of Emergency and Restorative Medicine. 13(1), 48-51.

Limonov, A.V., Zabrodin, V.V., Valiev, E.F., Zabrodin, E.V. (2014) Application of titanium mesh endoprosthesis for allotransplantation of inguinal hernias. Medical Bulletin of the Ministry of Internal Affairs. 1(68), 49-51.

Zhuravlev, V. A., & Kazakova, A. V. (2014). Methods of Mobile Teeth Splinting in Chronic Generalized Periodontitis Treatment (Review).Problems of Dentistry, (2) 4-8.

Kazakova, A.V., & Zhuravlev, V.P. (2014). Types of root splinting of mobile teeth in the complex treatment of chronic generalized periodontitis of severe degree. Medical Science and Education of the Urals, 15(4), 137-141.

Kolpakov, A.A., & Kazantsev, A.A. (2015). Comparative analysis of the results of application of the titan silk implant and polypropylene in patients with postoperative ventral hernias. Russian Medical Journal, (13).

Parshikov, V. V., Mironov, A. A., Anikina, E. A., Zaslavskaya, M. I., Alyokhin, A. I., & Kazantsev, A. A. (2015). Prosthetic repair of the abdominal wall using light and ultra-light synthetic and titanium-containing materials in high bacterial contamination (experimental study), CTM, 7(4).

Zhuravlev, V.P., Kazakova, A.V., & Kazantsev, A.A. (2015). Suture material titanell application in surgical chronic generalized periodontitis' treatment. Medical Science and Education of the Urals, (1), 79-82.

Magomedov M.M. and Magomedbekov R.E. (2015) Features of cytokine status in patients with inguinal hernias using endoprostheses, Journal of Cytokines and Inflammation, 14(4), 45-49.

Kazakova, A. V. & Zhuravlev, V. P. (2015). The feasibility of submucosal wiring method's application in periodontal flap surgery. Dentistry for everyone, 1, 14-16.

Kazantsev, A. A., Parshikov, V. V., Shemyatovsky, K. A., Alekhin, A. I., Titarov, D. L., Kolpakov, A. A., & Osadchenko, S. V. (2016). The titanium-containing mesh as a perspective group of implants for abdominal wall repair. Hirurgiia, (4), 86-95. Doi: 10.17116/hirurgia2016486- 95.

Parshikov, V. V., Mironov, A. A., Anikina, E. A., Kazantsev, A. A., Zaslavskaya, M. I., & Alyokhin, A. I. (2016). To the question about a possibility of use ultra-light titanium-containing mesh in abdominal wall repair in contaminated fields (experimental study). Hirugiia, 11, 64-70, doi: 10.17116/hirurgia20161164-70.

Ponomareva Y.V., Volova L.T., Belokonev V.I., Milyakova M.N., (2016) The role of the proteomic spectrum in predicting the biocompatibility of prosthetic materials, First All-Russian Congress of herniologists. Moscow, Oct. 27-28, 2016, 74-75.

Khodakov V.V., Zabrodin V.V., Zabrodin E.V. (2016) Evaluation of the effectiveness of inguinal hernia alloplasty with the use of titanium mesh endoprostheses. Medical Bulletin of the Ministry of Internal Affairs. 6 (85), 13-16.

Parshikov V.V., Kazantsev A.A., Mironov A.A., Zavaruev V.A., Chernikov A.N., Belayev O.F., Alyokhin A.I. (2016) Strength properties of abdominal wall in intraperitoneal and retromuscular repair using lightweight and ultra-lightweight synthetic and titanium- (56) References Cited

OTHER PUBLICATIONS containing endoprostheses (experimental study). Modern technologies in medicine, 8(3), 27-36. http://dx.doi.org/10.17691/stm2016.8.3.03.

Reshetov I.V., Starceva O.I., Istranov A.L., Vorona B.N., Lyundup A. V., Gulyaev I.V., Melnikov D.V., Shtansky D.V., Sheveyko A.N., Andreev V.A. (2016). Development of a three-dimensional biocompatible matrix for tasks of reconstructive surgery. Annals of Plastic, Reconstructive and Aesthetic Surgery, (2), 85-92.

Milyakova, M. N., Ponomareva, J. V., Gribkova, O. V., Sarbayeva, N. N., Limareva, L. V., & Bogush, V. V. (2016). Functional features of macrophages during the interaction with implants for hernioplasty. Technology of Living Systems, 10(8), 84-89.

Pechetov, A.A., Esakov, Y.S., Makov, M.A., Bazyluk, A. V., & Khlan, T.N. (2017). Combined Thoracoplasty in Total Postoperative Sternum Instability after Chronic Sternomediastinitis. High Technology Medicine, 4(4), 30-35.

Parshikov, V. V., Mironov, A. A., Kazantsev, A. A., & Alyokhin, A. I. (2017). Adhesions in the abdominal cavity after non-tension plasty with ultralight synthetic plastics nd titanium-containing endoprostheses. Modern technologies in medicine, 9(3), 45-54.

Nerobeev, A. I., & Kobazev, V. E. (2017). The use of titanium-containing mesh implants to eliminate ptosis of the soft tissues of the face in case of paralysis of the facial muscles. Clinical Dentistry, (2), 36-38.

Kazantsev, A. A., Tulyakov, S. S., Alekhin, A. I., Khoninov, B. V., Kazakova, A. V., Kozlov, N. A., Battaray, B., & Babichenko, I. I. (2017). Prospects for the use of polyfilament titanium suture material in traumatology. RMJ, 25(8), 533-538.

Starceva, O. I., Reshetov, I. V., Istranov, A. L., Vorona, B. N., Lyundup, A. V., Gulyaev, I. V., Melnikov, D. V., Shtansky, D. V., Sheveyko, A. N., & Andreev, V. A. (2017). Development of a three-dimensional biocompatible matrix in reconstructive surgery. Annals of Plastic, Reconstructive and Aesthetic Surgery, (1), 131-132.

Pivkina, S. I., & Kolesnikova, E. N. (2017). The knitting technology features for round-shaped integrally knitted implants made of titanium threads. In First Kosygin Readings. Kosygin State University of Russia.

Magomedov M.M., Magomedbekov R.E., Ismailov G.M. (2017) Systemic inflammatory response in alloplastic methods of inguinal hernia treatment. Journal of New Medical Technologies. Electronic edition. (2), 139-144.

Abalyan A.K., Aydemirov A.N., Mashurova E.V. (2017). First experience in using mesh endoprostheses made of Titanium Silk in the treatment of anterior abdominal wall hernias. In Proceedings of the II Congress of Herniologists, Moscow, 2017.

Alekhin, A.I., Shemyatovsky, K.A., Azimov, R.Kh., Kalinichenko, A.Yu., Glushkov, P.S., Yumatova, E.A., & Malyavko, V.A. (2017). Evaluation of the sizes and positioning of "Titanium Silk" implants using computed tomography after hernioplasty. II All-Russian Congress of Herniologists, Oct. 26-27, 2017, Moscow.

Parshikov, V.V., Chebotar, I.V., Anikina, E.A., Mironov, A.A., Kazantsev, A.A., & Alekhin, A.I. (2017). Biofilm process after implantation of ultra-light synthetic and titanium-containing endoprostheses under conditions of contamination with highly pathogenic microflora in experiment. II All-Russian Congress of Herniologists, Oct. 26-27, 2017, Moscow.

Kchibekov, E. A., Kokhanov, A. V., Kaliev, D. R., Kudaev, S. V., Bondarev, V. A., & Serdyukov, M. A. (2018) Features of inflammatory reaction of rats to implantation of modern mesh endoprosthesis for hernioplasty. Modern problems of science and education, (1), 61-61.

Reshetov, I. V., Starceva, O. I., Istranov, A. L., Vorona, B. N., Lyundup, A. V., Melnikov, D. V., Shtansky, D. V., & Sheveyko, A. N. (2018). Development of a 3D biocompatible composite matrix for reconstructive surgery of hollow organs and tissues. Annals of Plastic, Reconstructive and Aesthetic Surgery, (1), 99-100.

Karapetyan, G.E., & Cherepanova, T.V. (2018). Method of Surgical Correction of Defects of Front Angle Wall. Surgical Moscow Journal, 2(60), 47-51. doi: 10.17238/issn2072- 3180.2018.2.47-51.

* cited by examiner

TITANIUM MATRIX BASED ON A TENSION-FREE METAL WARP KNIT FABRIC FOR GUIDED TISSUE REGENERATION

CROSS REFERENCE TO RELATED APPLICATIONS

This nonprovisional application is a U.S. national stage application of International Application No. PCT/RU2018/000119, which was filed on Mar. 1, 2018, and is herein incorporated by reference.

FIELD OF THE INVENTION

The invention relates to medicine and, more particularly to surgery and oral surgery.

STATE OF ART

Various types of titanium membranes are known: resorbable and non-resorbable membranes. A disadvantage of resorbable membranes is their swelling when the bone defect is closed, which causes tension in the mucous membrane sutures covering said resorbable membranes, and in some cases to wound dehiscence resulting in infection of the wound and bone defect. Insufficient mechanical and skeletal function of the membrane results in prolapse of the central part of the membrane into the defect area and thus to a decrease in the volume of space required for filling with new tissue. The protein structure of collagen membranes is highly antigenic, which causes a subacute inflammatory reaction that occurs against the background of the material implantation. The elimination of said disadvantages of the membrane can be achieved by using perforated titanium foil as a membrane. This way, titanium membranes allow limiting the area that is subject to regeneration by keeping the space for bone formation and osteoplastic materials at the site of the defect, acting as a barrier. Due to the presence of laser microperforation, there is a circulation of fluids and oxygen in the membrane site, and the protective cells migrate freely between the clot and the flap. The membranes are stabilized with special titanium screws, which requires careful suturing of the mucosal flaps to completely close the membrane. Usually, the membranes are removed 6-8 μmonths after the complete formation of the necessary volume of bone tissue. The disadvantages of perforated titanium membranes are excessive rigidity, and sharp edges, which often cause trauma to the mucous membrane, tissue dystrophy above the membrane, wound dehiscence, and partial necrosis of the mucoperiosteal flap. The lack of porosity and the structure rigidity do not allow this material to integrate into the tissue and require repeated operation in order to remove thereof.

A device for guided regeneration of bone tissue made of titanium fiber (RU128098 U1, publ. 20 May 2013) is known. The device for guided regeneration of bone tissue consists of a membrane in the form of a sponge, obtained as a ring with a thickness, wherein a mesh plate consisting of wire titanium threads with a diameter of 0.1-1.5 mm, covered with calcium-phosphate ceramics, has a hole corresponding to the dimensions of the cervical part of the tooth, while a wire titanium fiber with a diameter of 0.5-2 mm having two free ends is located around the hole, consists of a mucous membrane, soft tissues, and bone, this solution can be applied to the shaping of the latter. When using such a material, contact between titanium threads with a diameter of 0.1-0.15 mm and the mucous membrane should be avoided due to the risk of perforation of the latter. All these disadvantages are associated with excessive thickness, and therefore, with the elasticity of the titanium thread used by the authors of the solution. The specified thickness of the titanium thread allows obtaining a porous material by the weft-knitting method only, that is, the material is knitted from one thread, has limited elasticity, a tendency to unraveling when cut, while the excessive weight and rigidity of loops made of a thread of said diameter can create risk of mechanical trauma to the mucous membrane and gum tissue. In this design, titanium ceramics provides additional rigidity to the titanium threads.

Also known is a braided titanium nickelide membrane having shape memory for guided tissue regeneration, which membrane is in the form of a mesh plate, consisting of super-elastic threads with a diameter of 50-60 μm made of TH-10 alloy, which are braided by textile technology, wherein a distance between adjacent threads is 100-200 μm, and wherein the plate is bent along the shape of the ridge of the alveolar process and retains the given shape due to the memory effect (RU117087 U1, publ. 20 Jun. 2012). Disadvantages of this design are that the material consists of titanium nickelide, which has suboptimal biological inertness. A disadvantage of the known device is the use of titanium nickelide as a titanium alloy. The implant described by the authors is a mesh plate (a body bounded by two parallel planes, the distance between which, called the plate thickness h=const, is small compared to its other dimensions). Based on this, the free movement of interstitial fluid and tissue outgrowth is possible only in one direction (up/down), while the movement of fluid and tissue outgrowth also in the transverse direction is limited by the geometric feature. It should be noted that the same property negatively affects the drainage of the postoperative wound, delaying wound discharge and creating conditions for wound infection.

The closest in technical essence is a titanium mesh implant (RU121735 U1, 10 Oct. 2012), manufactured by OOO NPF "TEMP" under the trade name "Titanium silk", which is made of VT 1-00 alloy having a titanium content of more than 99%, with a thickness of the thread used of 0.03-0.25 mm, wherein said implant has good biocompatibility with tissues, causing no toxic, allergic and other adverse reactions when being implanted. The material has proven itself to be good in surgically shaping, being made with the possibility of implantation into some soft tissues. Among the varieties of metal knitted fabric presented for the production of implants, the most promising is warp-knitted metal fabric made from threads of 65 μm. The mesh fabric made from said threads has a significant elasticity of 45-70%, a minimum surface density of 40-45 g/m$^2$, and also a high porosity of the material, reaching 92%. Additionally, the structure of the warp-knitted fabric has a pronounced three-dimensionality, which can also be controlled in a wide range, thus creating not only the width and length of the material, but also the thickness even when knitted in one layer. The material can be successfully used in surgically shaping of the skin, subcutaneous fat, adipose tissue, muscles, aponeuroses, fascia, and in the intermuscular connective tissue. The biological inertness of the material is guaranteed by the use of GRADE 1 and GRADE-5 titanium alloys (Russian analogues of VT1.00, VT1.00 wa, and VT6). The disadvantage of this material is the presence of elastic (resilient) deformation in the material, which inevitably occurs when the material is stretched. As a result, the obtained mesh can deform, twist, form folds and put pressure on adjacent structures, causing tension of the body tissues to which it is sewn. As a result of elastic deformation present in the material, pressure ulcer development in the tissues, cheese-wiring of the material through delicate structures, tearing the mesh from the suture material, and implant wrinkling can take place. This limits the use of the material in such an area of delicate surgically shaping as the oral mucosa. Said disadvantages limit the indications for use of the material in surgery for guided tissue regeneration, creating a risk of cheese-wiring the material through or perforating the mucous membrane with individual threads of the titanium mesh.

The claimed invention makes it possible to substantially overcome the indicated disadvantages inherent in the prototype.

DISCLOSURE OF THE INVENTION

The technical problem that the proposed technical solution solves is the development of a titanium matrix that improves the results of surgery for guided tissue regeneration of the alveolar process, which material possesses the necessary physical and mechanical properties.

The technical result consists in a decrease in the elasticity and an increase in the plasticity of the matrix, allowing the set dimensions of an implant to be preserved after the removing all loads on the material; an increase in the adhesion of the matrix to the wound bed; delineation of the growth of the mucous membrane and of the bone tissue; good quality formation of the necessary volume of bone tissue for the subsequent insertion of dental implants; minimal likelihood of biomechanical incompatibility between the knitted fabric and the mucous membrane; and reduced risk of trauma.

The technical result is achieved due to the fact that the titanium matrix based on tension-free metal knitted fabric for guided tissue regeneration is made of warp-knitted mesh fabric, knitted from titanium threads, while the structure of the mesh fabric is made in the form of a combined, plain, two-bar metal knitted fabric formed on the basis of primary and derived weaves and having alternating wales consisting of one and two titanium threads respectively, wherein the titanium threads have a contoured surface.

An oxide film is applied to the surface of the contoured titanium threads.

The oxide film has a thickness of 0.3-3 μm.

Titanium threads has a diameter of 20-80 μm.

The contoured surface of titanium thread is made with a varying titanium thread diameter with a fluctuation of 1-10 μm.

The mesh fabric is made with a loop module of 70-300.

Metal knitwear has a cell size of not more than 2 mm.

Titanium threads are made from GRADE-5 alloy.

IN THE FIGURES, THE POSITIONS INDICATE

Figure 1:
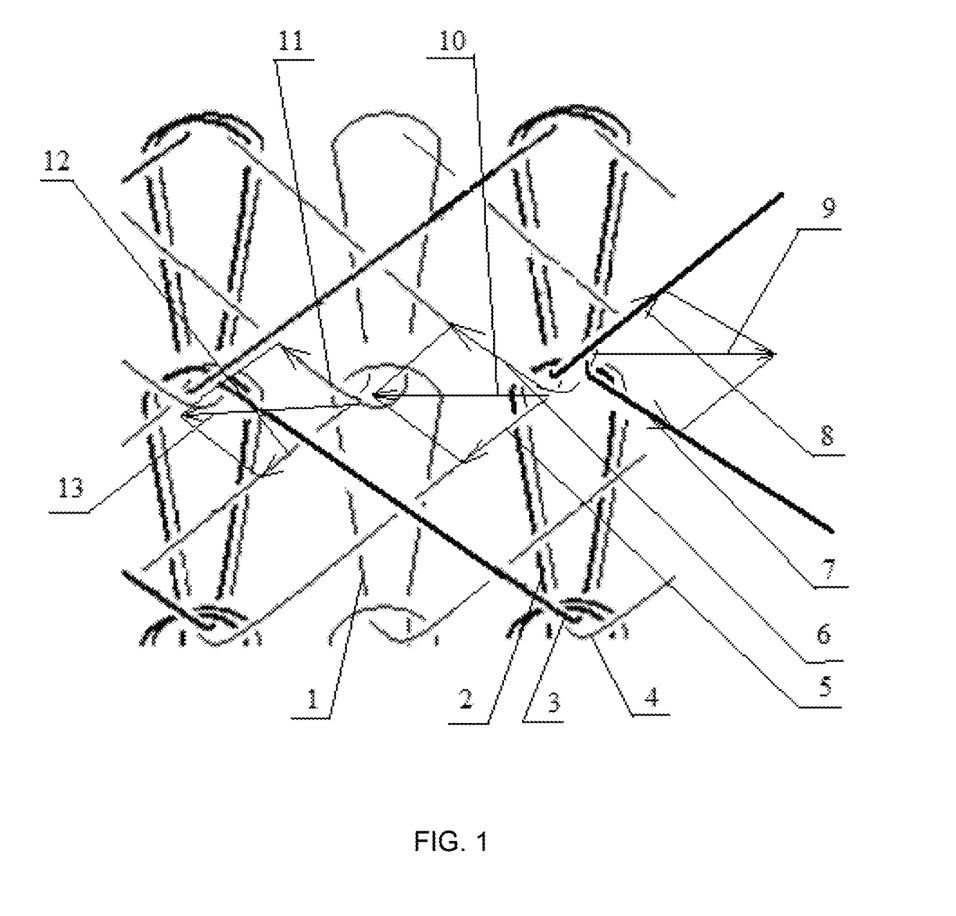
FIG. 1. A view of combined warp-knitting weave.
Figure 3:
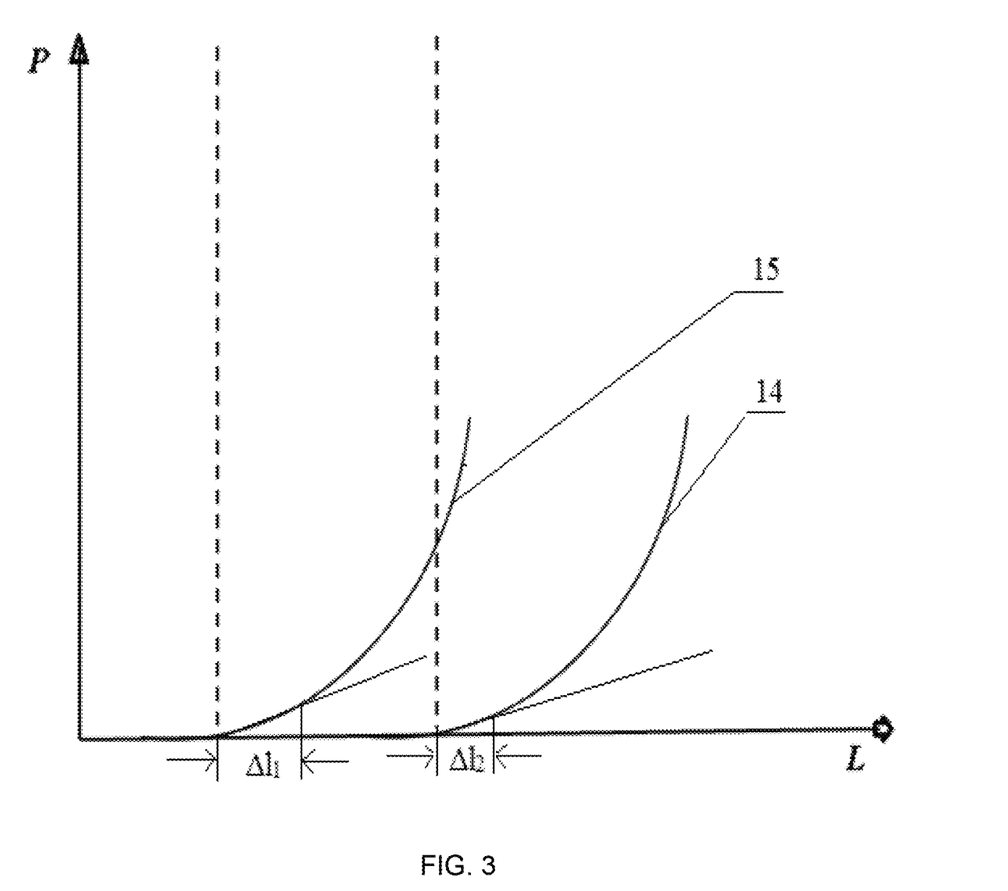
FIG. 3. Stretching graphs of titanium metal knitted fabrics.

1—wales consisting of one thread;
2—wales consisting of two threads;
3, 4—interloop floats directed in different directions;
5, 6, 7, 8—compression forces for loops consisting of two threads;
9, 10—total compression forces for loops consisting of two threads;
11, 12—compression forces for loops consisting of one thread;
13—total compression force for loops consisting of one thread.
14—stretching graph of the proposed material for the titanium matrix;
15—stretching graph for the "Titanium silk" material.

Embodiments of the Invention

The matrix is designed for guided tissue regeneration, for example, in the alveolar process, and made of a warp-knitted mesh fabric with a thickness of 0.08-0.32 mm having a loop module of 70-300, which fabric is knitted from titanium threads with a diameter of 20-80 μm. The structure of the fabric is made in the form of a combined, plain, two-bar metal knitted fabric, formed on the basis of the primary and derived weaves and having alternating wales 1 and 2 (FIG. 1), consisting of one and two titanium threads respectively. The threads can be made of VT1-00, VT-1.00 wa (GRADE-1) or VT6 (GRADE-5) titanium alloys. The titanium threads used provide high biological inertness and plasticity of the threads, allowing to avoid trauma to tissues.

The structure of the fabric does not have filet openings, which provides less stretchability of the fabric, which is important both during the formation of the matrix and during its work in the postoperative period. The number of interloop floats 3 and 4 (FIG. 1) directed in different directions will be different, while the number of floats for loops consisting of two threads is twice as large as for loops consisting of one thread, four and two respectively. Moreover, the floats and the tensile and compressive forces 5, 6, 7, 8 (FIG. 1), in loops consisting of two threads are directed in different directions, which results, after removing the tensile force, in balancing the total compressive forces 9, 10 (FIG. 1). Compressive forces 11, 12 (FIG. 1) in loops consisting of one thread create a total compressive force 13, which turns out to be insufficient for the shrinkage of the knitted fabric, which is explained: firstly, by plastic deformations that occur during stretching of the metal knitted fabric, due to the overstretching of the thread from the loop skeletons into floats; secondly, by the presence of at least sixteen points of contact between the loops consisting of two threads, with floats, which makes it impossible to overstretch the threads into tightened loops reduced when stretching.

Figure 2A:
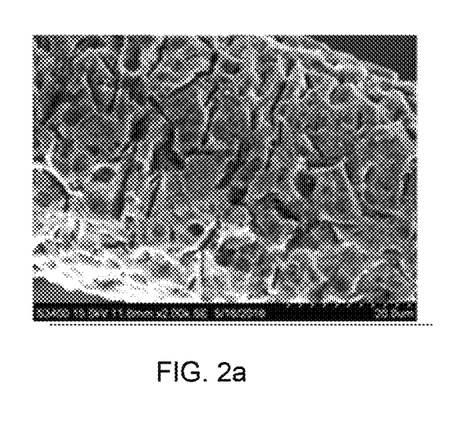
FIG. 2a. Example of a surface relief of the thread after chemical etching.
Figure 2B:
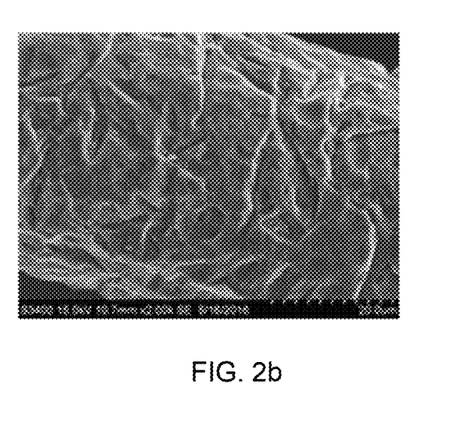
FIG. 2b. Example of a surface relief of the thread after ionic treatment.

Also, another important factor is to provide tension-free properties to the knitted metal fabric (stress removing in the area of the loop contact), by obtaining contoured surface of titanium threads in the form of chaotically spreading depressions and bumps (FIGS. 2a and 2b), with a general decrease in the thread diameter of the knitted fabric thread resulting in a decrease in the contact area of the loops.

Technological processes that make it possible to obtain tension-free metal knitted fabric with a contoured surface of the titanium thread are: power ultrasonic treatment, chemical etching, electrochemical polishing, ion treatment, etc. These methods of treatment reduce the diameter of the titanium thread already in the structure of the knitted fabric by 10-35% of the original diameter, while simultaneously reducing the area of interloop contacts and removing stresses in the area of interloop contacts, thereby eliminating elastic properties and increasing the plasticity of metal knitted fabric, while forming a porous structure with high adhesion to the wound surface. As a result, a "telescopic effect" is obtained: the penetration of loops and interloop floats into the area of adjacent loops. This effect is not observed on untreated (native) metal knitted fabric.

The tension-free properties of the metal knitted fabric solve the problem of residual elasticity, and the telescopic effect provides easy straightening of the fabric.

Thus, FIG. 3 shows stretching graphs of the proposed material and the "Titanium silk" material 14 and 15, where P shows the tensile force, and L is the elongation of the stretched materials. The graphs show that plastic deformation of the proposed material 14 occurs earlier than in the sample of the "Titanium silk" material 15, since the elongation $\Delta l2 < \Delta l1$, which confirms the decrease in elastic deformations in the proposed matrix material. In the proposed material, the percentage of elastic (resilient) deformations is 35-40%, while for the "Titanium silk" material, the specified elasticity is 45-70%.

Figure 4:
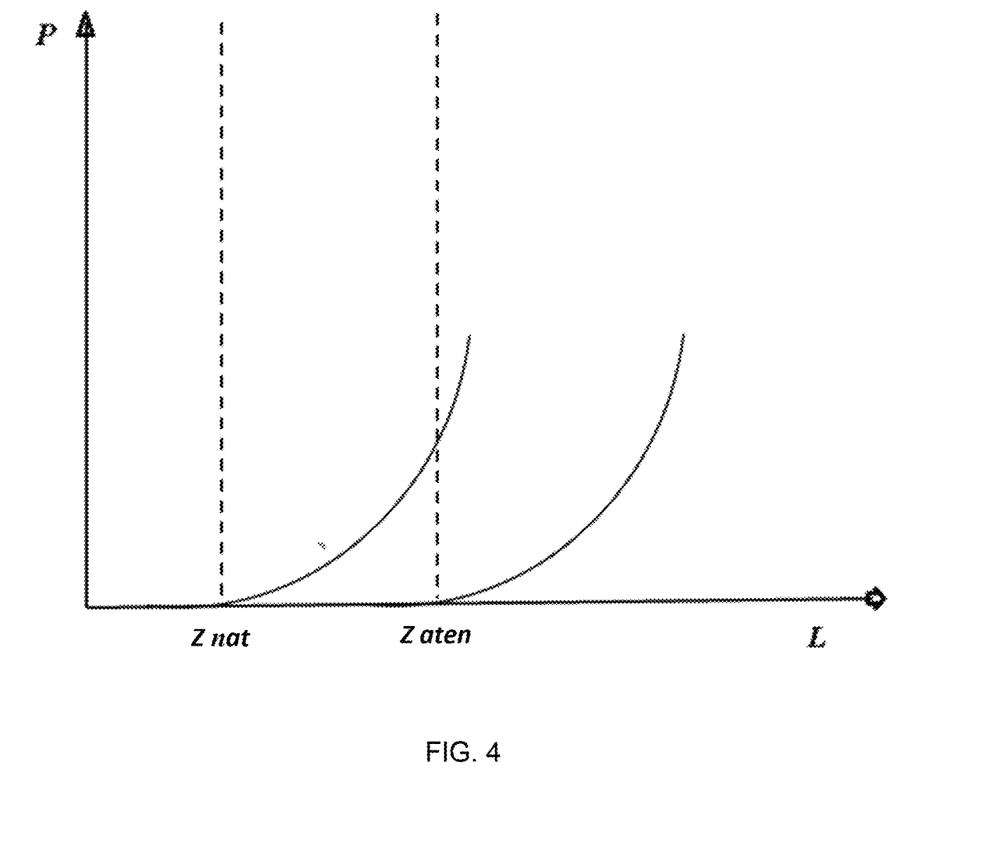
FIG. 4. Graph of zero tensile rigidity for knitted meshes.

Also, when stretching knitted meshes, there is a period of zero rigidity Z (FIG. 4), that is the area on the diagram where the mesh fabric is stretched without resistance, where Z aten is zero rigidity of the tension-free metal knitted fabric with contoured threads, and Z nat is zero rigidity of the native metal knitted fabric with uncontoured threads. When comparing native and tension-free metal knitted fabric of the same type of knitting and thread thickness, it is determined that the area of zero rigidity of tension-free metal knitted fabric is 20% or more larger than that of the native material.

Figure 5A:
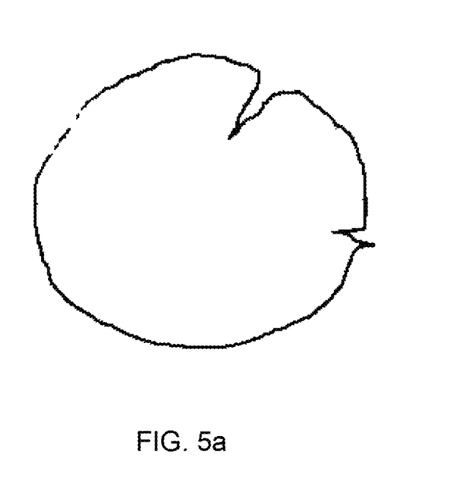
FIG. 5a. Cross-section of a thread with longitudinal sharp-pointed defects before the treatment.
Figure 5B:
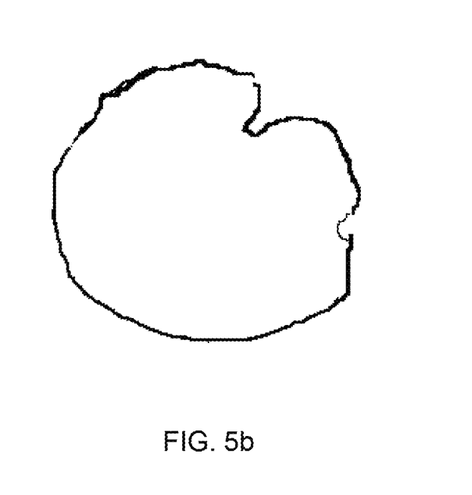
FIG. 5b. Cross-section of a thread with smoothed longitudinal defects after the treatment.

In addition, in the structure of the tension-free mesh fabric, scuff points in the form of longitudinal grooves (FIG. 5a) arising on the surface of the thread from the drawing of the thread are smoothed in the process of treatment, for example, by electrochemical polishing. Smoothing of defects after the treatment is shown in FIG. 5b. Smoothing of longitudinal defects, which are the concentrators of internal stress, harmonizes the residual stress in the thread itself and reduces the risk of the mesh fabric breakage.

Treatment also results in the creation of the varying diameter of the titanium thread with fluctuations along its length from 1-10 µm, which also results in additional freeness of interloop gaps.

To further increase the plasticity, an oxide film with a thickness of 0.3 to 3 µm can be applied to the surface of the tension-free metal knitted fabric. It is known that the application of titanium oxide results in a decrease in the sliding friction coefficient by about 3 times and significantly increases the dynamism of the tension-free metal knitted fabric, allowing the loops to easily slide relative to each other, that positively affects the extensibility of the material. The surface oxide film reduces the friction between knitted loops, and also the accompanying negative properties: breakage when the material is straightened, etc.

The oxide film is obtained by immersing mesh fabric made of contoured threads into a galvanic bath filled with the necessary solution, with a constant current, for a certain time. Depending on the time and the selected voltage, an oxide film with a thickness of 0.3-3 µm is formed on the surface of the titanium thread. In this case, the thickness of the thread itself does not increase.

A substantive property of the oxide film is the possibility of its obtaining in different colors, which depends on the thickness of the oxide layer. Control of the metal knitted fabric color allows the color of metal knitted fabric to be adjusted closer to the color of the mucous membrane, improving the cosmetic effect when the implant from metal knitted fabric is installed.

The use of a weave in the warp-knit material, which weave is a structure of a combined, plain, two-bar knitted fabric based on primary and derived weaves and having alternating wales in the fabric structure, which wales consist of one and two threads, results in the stabilized structure, a decrease in the stage of elastic deformations and an early transition to plastic deformations that allow the set dimensions of an implant shape to be preserved after the removal of all loads.

The knitted metal knitted fabric has a cell size of no more than 2 mm, which is an additional factor for retaining bone filler material.

Providing tension-free properties to the material fully solves the problem of permanent elastic deformation. The resulting telescopic effect provides a long period when the fabric stretches without resistance.

The high plasticity of the warp-knitting material obtained eliminates the possibility of biomechanical incompatibility between the knitted fabric and the mucous membrane and allows the material to be placed under the mucous membrane even in the case of extremely thin mucous membrane. In contrast to the titanium mesh implant "Titanium Silk", the titanium matrix expands freely over the surface of the surgical wound and provides a pronounced adhesion to the surface of the surgical wound; it easily assumes and retains the given shape, and can be modeled according to the shape of the surgical wound by stretching, if necessary.

The porosity of the material provided by the presence of free space between the loop rods and loop floats, increases the rate of penetration of biological fluids inside the implant, accelerates the process of its colonization with fibroblasts and osteoblasts and improves the integration of the material; being in contact with the wound surface, the titanium matrix is instantly impregnated with blood and wound discharge and exhibits pronounced adhesion to the wound surface, providing temporary self-fixation and allowing the surgeon to avoid using fixing elements: pins, micro-screws, etc.

The high adhesion of the titanium matrix made of the tension-free metal knitted fabric to the wound surface allows the titanium mesh to be placed without causing tension of the mucoperiosteal flap, preventing such a frequent complication as the surgical wound dehiscence. At the same time, the highly porous structure does not delay the wound discharge, eliminating the likelihood of fluid leaks and subsequent infection thereof.

The contoured surface of the thread significantly improves the fixation of fibrin fibers thereon, thereby facilitating the attraction of fibroblasts serving as a source of newly formed connective tissue.

If necessary, the titanium matrix of any required size can be formed, for example, 2*2; 2*3; 3*3 cm, etc.

Easy cutting of the implant after the formation of the bone layer is also an important feature. Thus, it allows dental implants to be inserted without removing the titanium matrix, which is not possible when using a perforated titanium foil as the titanium membrane.

The technique of guided tissue regeneration operations is based on the principle of separation of the bone surface from soft tissues thereon in the area of the bone defect and the intended site of the insertion of a dental implant in the alveolar process of the upper or lower jaw. Such separation is carried out by physically separating the anatomical structures (part of the gum from the bone or implant) from each other with a porous titanium matrix having form of a thin titanium mesh.

Preoperative planning in persons who have indications for guided tissue regeneration surgery, for example, in the alveolar ridge, consists in measuring the size of the tissue defect to be covered with a titanium matrix. The method for guided tissue regeneration involves the use of a delineating membrane and granules of xenogenic or allogeneic hydroxyapatite, as well as, in many cases, autogenous bone chips. The technique of the surgery for guided tissue regeneration when replacing a bone defect is as follows. The horizontal incision line on the mucous membrane is usually drawn along the ridge of the alveolar process. A revision of the tissue defect is performed, which defect is filled with granules of bone-replacement material, xenogenic bone crumbles and/or autologous bone. Then the formed complex is covered with a titanium matrix, which is laid under the mucous membrane. It is allowed to close the defect only using a titanium matrix, for example, to eliminate gingival pockets. The operation ends with suturing of the mucous membrane and applying a gingival bandage. Trichopol is prescribed for 5-7 days, with careful oral hygiene. Membrane localisation between the flap and the root surface favors the repopulation of the periodontal ligament cells on the root surface. The claimed technical solution makes it possible to eliminate the swelling of the wound edges and wound dehiscence, provides ergonomical technique of surgery for guided tissue regeneration, to ensure reliable fixation of the bone replacement material throughout the tissue defect, thereby restoring the anatomical integrity of this area. The use of ultra-light titanium matrix made of tension-free metal knitted fabric makes it possible to decrease the rate of complications and improves the result of the surgery by reducing the antigenicity and increasing the biocompatibility of the material. The use of said matrix eliminates the need for its revision before insertion of a dental implant due to easy cutting of holes for implants, and the nature of the material designed for long-term presence of the material in the body. The effectiveness of the use of the claimed matrix is confirmed by a number of clinical observations.

Example 1

Patient E., 46 years old, diagnosed with moderate generalized periodontitis. Local recession measuring 6 mm in the canine area of the upper jaw. After professional hygiene and sanitation of the oral cavity, the patient underwent a flap operation on the upper jaw in the area of 5-12 teeth using the Ramfjord technique. After detachment of the mucoperiosteal flap, curettage of bone pockets was performed with removal of granulation tissue and treatment of the root surfaces of 5-12 teeth, then using a special bur, the bone tissue was processed. Taking into account the pronounced defect of the alveolar bone and the absence of a significant part of the compact plate, the bone defect was filled with osteoplastic material and covered with a titanium matrix made of tension-free warp-knitted metal knitted fabric made of titanium threads 20 µm in diameter and having a loop unit of 70, with a cell size of 0.7 mm. 2.5 µmonths after the operation, the restoration of the alveolar process was determined by X-ray examination. After the second stage of the operation, the necessary volume as well as sufficient density of bone tissue were restored. The insertion of dental implants was performed as usual.

Example 2

Patient D., 50 years old, diagnosed with generalized periodontitis. Local recession of soft tissues of the gums measuring 9 mm in the canine area of the upper jaw. After professional hygiene and sanitation of the oral cavity, the patient underwent a flap operation and after detachment of the mucoperiosteal flap, curettage of bone pockets with removal of granulation tissue and treatment of the root surfaces of 14-16 teeth using the Piezon-Master apparatus were performed. Osteoplastic material was placed under the mucous-gingival flap, after which it was covered with a porous matrix of the tension-free warp-knitted titanium metal knitted fabric, knitted from titanium threads 80 µm in diameter, with a loop module of 300 and a cell size of 1 mm. After the surgery, the restoration of the soft tissues of the gum and the closure of the necks of the teeth with soft tissues were determined. After 3 µmonths, the patient was invited to the second stage for the insertion of dental implants, the bone tissue was fully restored, and the formation of the dental implant bed took place without difficulty.

The technical solution consists in adjustment of the titanium mesh for placing under the mucous membrane by increasing plastic properties of the said mesh by combining a special textile weave and providing it with the tension-free properties.

The claimed titanium matrix obtained from titanium threads by warp knitting, in the form of a combined, single plain, two-bar knitted fabric, formed on the basis of primary and derived weaves and having alternating wales, consisting of one and two threads respectively, has stabilized structure, having a shorter period of plastic deformation of the structure, which allows the set dimensions of an implant to be preserved after the removal of all loads on the material. Due to the high plasticity of the warp knit material obtained, the likelihood of a biomechanical incompatibility between the knitted fabric and the mucous membrane is eliminated, allowing the material to be placed under the mucous membrane without risk of trauma to the oral cavity or pressure ulcer development on the mucous membrane.

The use of the titanium matrix having tension-free properties with low elasticity and increased plasticity for guided tissue regeneration results in an increase in the adhesion to the wound bed, delineation of the growth of the mucous membrane and of the bone tissue, allows the mucoperiosteal flap to be laid without tissue tension, provides good vascularization and integration of the titanium matrix, resulting in good quality formation of the necessary volume of bone tissue for the subsequent insertion of dental implants, which ultimately leads to an improvement in the results of the surgery for guided regeneration of periodontal tissues arising from inflammatory and degenerative processes and is an effective solution to the problem of bone tissue deficiency, for example, in the alveolar process of the upper or lower jaw.

We claim:

1. A titanium matrix based on a tension-free metal knitted fabric for guided tissue regeneration, wherein said matrix is made of a warp-knitted mesh fabric knitted from titanium threads,
    wherein the mesh fabric comprises a structure having alternating wales consisting of one and two titanium threads, respectively, and
    wherein the titanium threads have a relief surface.

2. The titanium matrix according to claim 1, wherein an oxide film is applied to the relief surface of the titanium threads.

3. The titanium matrix according to claim 2, wherein the oxide film is 0.3-1 μm thick.

4. The titanium matrix according to claim 1, wherein the diameter of the titanium threads is 20-80 μm.

5. The titanium matrix according to claim 1, wherein the surface relief of the titanium threads is made with a varying diameter of the titanium threads.

6. The titanium matrix according to claim 5, wherein the surface relief of the titanium threads is made with a varying diameter of the titanium threads with a fluctuation of 1-10 μm.

7. The titanium matrix according to claim 1, wherein the mesh fabric is made with a loop module of 70-300.

8. The titanium matrix according to claim 1, wherein the metal knitted fabric has a cell size of not more than 2 mm.

9. The titanium matrix according to claim 1, wherein the titanium threads are made of GRADE-5 alloy.

* * * * *